United States Patent [19]

Flick

[11] 4,233,743
[45] Nov. 18, 1980

[54] SKIN-FOLD CALIPER

[75] Inventor: Francis S. Flick, Oakbrook, Ill.

[73] Assignee: Health & Education Services Corporation, Bensenville, Ill.

[21] Appl. No.: 765,090

[22] Filed: Feb. 3, 1977

[51] Int. Cl.³ .............................................. G01B 3/38
[52] U.S. Cl. .............................. 33/143 C; 33/143 M; 33/174 D
[58] Field of Search ............ 33/143 R, 143 M, 143 F, 33/143 C, 174 D

[56] References Cited

U.S. PATENT DOCUMENTS

| 1,357,323 | 11/1920 | Jaques | 33/147 F |
| 1,958,024 | 5/1934 | Stowell | 33/143 M |

Primary Examiner—Willis Little
Attorney, Agent, or Firm—Wegner, Stellman, McCord, Wiles & Wood

[57] ABSTRACT

A skin-fold caliper includes a base member having a handle portion and a jaw portion, a slide member having a mounting portion and a jaw portion, and a coiled spring attached between the base member and the slide member to bias the ends of the respective jaw portions together. The slide member is mounted within a recess defined by the base member for linear movement therealong. The spring is selected so that a change in its extended length does not effect a large change in the force applied to close the jaws. Herein, a thin wire spring with many coils housed between the base member and slide member is utilized to obtain this function.

2 Claims, 2 Drawing Figures

U.S. Patent  Nov. 18, 1980  4,233,743
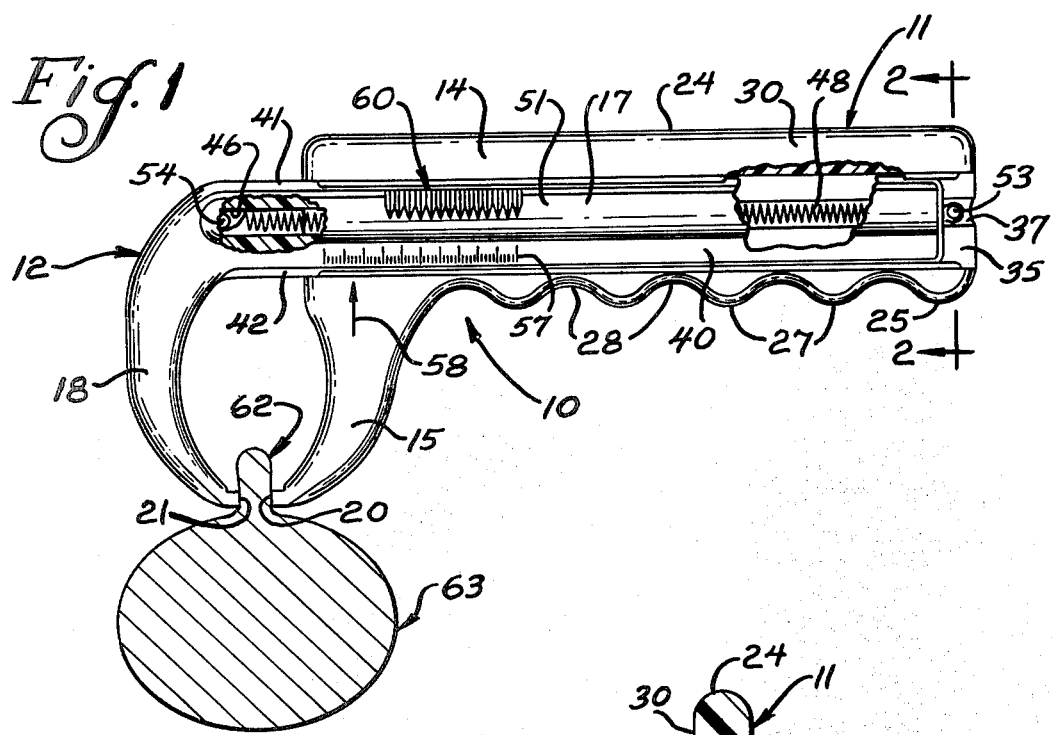
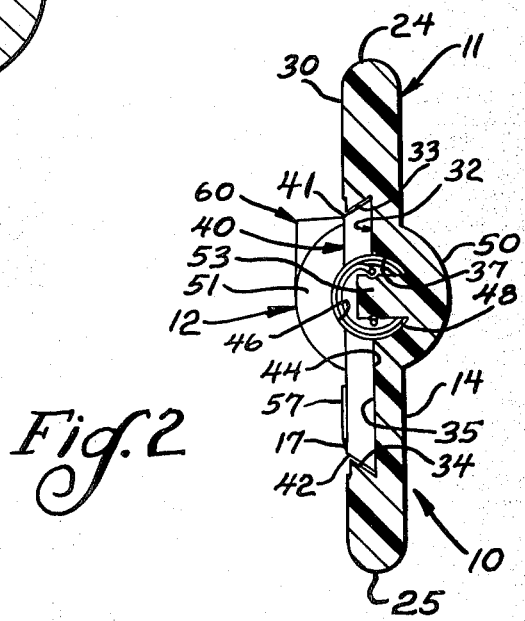

SKIN-FOLD CALIPER

BACKGROUND OF THE INVENTION

This invention relates generally to a caliper and, more particularly, to a skin-fold caliper of simple construction in which the jaws thereof are biased together by a spring.

Although this invention has particular application in the field of bariatric medicine for the study and treatment of obesity, it can be appreciated that its use need not be so limited. The caliper disclosed herein can be utilized by physiologists and bariatricians to determine what percentage of the human body is fat and what percentage is actually vital body tissue and muscle. An accepted technique for determining the percentage of fat has been to measure the hydrostatic weight (underwater weight) of the person under study. However, weighing a person underwater can be extremely inconvenient.

It is widely known that the human body stores 50 percent or more of its fat under the surface of the skin and that as the percentage of total fat increases, the thickness of the subsurface layers of fat increases in substantially equal proportion. Thus, if assessments are made of the subsurface layers by measuring the thickness of skin folds, it is possible to estimate the total amount of fat accumulated by the body.

Typically, skin-fold measurements are taken by pinching the skin and the flexible subtissue below the skin at certain selected positions on the body and the limbs. For women, these measurements can be taken at the back of the arm (tricep) and at the hip (iliac crest). For men, additional measurements may be taken at the front of the arm (bicep) and at the upper back (subscapular). The sum of these measurements is then compared with a chart to determine the relative percentage of fat.

It should be evident that because of the resiliency of the skin and the subsurface layer of fat, the measurements obtained will necessarily be a function of the pressure applied by the caliper. The generally accepted standard pressure for taking skin-fold measurements of the human body is 10 grams per square millimeter.

Presently, constant pressure calipers designed to measure skin folds are available, one such device is illustrated in Lange U.S. Pat. No. 3,008,239. However, this device is relatively complex and, therefore, prohibitively expensive. The Lange calipers utilize a spring to apply pressure between the jaws thereof. However, since a spring generates a force which varies proportionately with the distance to which it is extended, Lange employs a gear and lever system to obtain constant pressure over the range of distances through which the jaws may be extended.

By constructing a caliper having jaws which move linearly away from each other and by employing a coiled tension spring having desirable design parameters, a caliper can be simply and inexpensively manufactured. It has been found that slight pressure changes do not significantly affect the accuracy of skin-fold measurements particularly where skin-fold thickness is, in practice, only an approximation of actual fat accumulation. Therefore, a linear spring-operated caliper capable of taking relatively accurate measurements is feasible provided that the spring is appropriately selected so that changes in spring extension effect only insignificant changes in applied spring force.

SUMMARY OF THE INVENTION

It is the principal object of the invention to provide a skin-fold caliper which is relatively inexpensive and operates with insignificant changes in pressure.

In accordance with the invention, a skin-fold caliper includes a base member having an elongate handle portion and a jaw portion at one axial end, a slide having a mounting portion positioned adjacent the handle portion movable axially therealong and a jaw portion which cooperates with the jaw portion of the base member, and a tension spring having one end attached to the base member and its other end attached to the slide member to urge the jaws closed. The tension spring is a coiled thin wire spring of many turns in which the variation in pressure at extended positions is not great enough to adversely effect skin-fold measurements.

In an exemplary embodiment of the invention, the handle portion of the base member and the mounting portion of the slide member define an axially-extending recess in which the spring is disposed. The handle portion also has an axially-extending dovetailed channel and the mounting portion has a cross-sectional configuration adapted to slide within the dovetailed channel. This provides a means for slidably mounting the slide member on the base member so that the jaws may be moved to an extended open position by manual operation and moved to a retracted closed position by spring pressure.

A linear scale is provided on one of the slide member and the base member and an indicator is juxtaposed on the other so that visual identification of the distance between the jaws may be made, thereby providing an indication of the thickness of a skin fold which is clamped between the nibs of the jaws under spring pressure.

The skin-fold caliper disclosed herein has two components which are closed together by a spring. These two components may be formed from plastic by injection molding so that an inexpensive caliper may be constructed which provides a measurement of skin-fold thickness sufficient to estimate the percentage of fat within the human body.

BRIEF DESCRIPTION OF THE DRAWINGS

FIG. 1 is a side elevational view of a caliper constructed in accordance with the invention partially broken away to illustrate the internal position of the spring and showing the caliper measuring a skin fold; and FIG. 2 is a cross-sectional view taken along line 2—2 of FIG. 1 illustrating the interconnection between the base member and the slide member and the position of the coiled spring.

DESCRIPTION OF THE PREFERRED EMBODIMENT

In the drawings, the skin-fold caliper, generally designated 10, is seen to be comprised of a base 11 and a slide 12. The base 11 is comprised of an elongate handle portion 14 and an arcuate jaw portion 15 extending laterally outward from the handle portion 14 at one axial end thereof. The slide 12 is comprised of an elongate mounting portion 17 laterally adjacent the handle portion 14 and an arcuate jaw portion 18 at one axial end of the mounting portion 17 extending laterally outward from the mounting portion 17 in the same direction as the jaw portion 15 extends from the handle portion 14.

As seen in FIG. 1, the jaw portion 18 is positioned axially outward from the jaw portion 15. The jaw portions 15 and 18 have respective end tips or nibs 20 and 21. The surface of the nib 20 faces axially outward while the surfce of the nib 21 faces axially inward so that the nibs 20 and 21 are opposed and may be opened and closed relative to each other so as to modify the distance therebetween.

The base 11 is generally flat and (in the position illustrated) has a rounded upper edge 24 and a smoothly rounded lower gripping edge 25, the latter including a series of ridges 27 and valleys 28 configured to conform with the fingers of the operator's hand. A lateral surface 30 is generally planar with a cut-out space or mortise, generally designated 32, defined by outer bevels 33 and 34 and bottom planar surface 35. Formed in the planar surface 35 is an axially-extending channel or recess 37 having a semicircular cross section.

The mounting portion 17 of the slide 12 has a wedge-shaped tenon, generally designated 40, which is defined by an inner bevel 41 at the rearward edge, an inner bevel 42 at the forward edge, and a bottom planar surface 44 adapted to slide lengthwise along the planar surface 35. As a result, there is a interlocking dovetailed connection between the base 11 and the slide 12. The mortise 32 and the tenon portion 40 extend axially on the respective base 11 and the slide 12 so that the slide 12 may be moved linearly relative to the base 11 to axially open and close the jaw portions 15 and 18 and therefore the respective nibs 20 and 21.

Formed in the planar surface 44 of the slide 12 is an axially-extending channel or recess 46 having a semicircular cross section and being disposed relative to the recess 37 of the base 11 to define a circular housing for a coiled tension spring 48. The handle portion 14 and the mounting portion 17 have elongate, arcuate, axial walls 50 and 51, respectively, to accommodate the respective recesses 37 and 46. The coiled spring 48 has one end attached to a lug 53 carried by the handle portion 14 within the recess 37 at the end opposite the jaw portion 15. The other end of the spring 48 is attached to a lug 54 carried by the mounting portion 17 within the recess 46 at the end from which the jaw portion 18 extends. The spring 48 thus urges the lugs 53 and 54 together to bias the jaw portions 14 and 15 to a retracted closed position.

The force applied by a spring is generally proportional to its displacement, i.e., $F=k \cdot s$, where k is the so-called "spring constant." The constant k is proportional to the wire diameter, is inversely proportional to the mean coil diameter and the total number of active coils (turns), and is dependent on the spring material. If a spring is chosen having a relatively small k, then changes in displacement will not substantially change the applied force. By selecting a spring such as a thin wire spring with many turns, the constant k will be small.

Herein, the coiled tension spring 48 is formed from wire 0.014 inch thick wound in a coil having an outside diameter of 0.25 inch and a collapsed length of 1.2 inches. Hence, the spring 48 has about 85 active coils and a k roughly equal to 28 grams per inch. Because the spring constant k is small, the spring 48 must be stretched substantially to achieve the initial desired pressure of 10 grams per square millimeter. When the caliper 10 is in a closed retracted position, the nibs 20 and 21 being engaged, the spring 48 is stretched to a length of about 6.5 inches and generates a spring force of approximately 150 grams. Each of the confronting surfaces of the nibs 20 and 21 has a surface area of approximately 15 square millimeters. Consequently, when the caliper 10 is closed, the pressure between the nibs 20 and 21 is approximately 10 grams per square millimeter. It is evident that a greater nib surface area will result in a decrease in applied pressure. The nibs 20 and 21 may thus be made larger or smaller as desired with a corresponding alteration of the spring.

When a spring of this type is extended slightly, such as by opening the jaws, spring pressure is not substantially altered. For example, a distance of 1 inch between the nibs 20 and 21 causes an increase in pressure of about 2 grams per square millimeter, an amount which is not great enough to adversely affect skin-fold measuring results. Smaller pressure changes could obviously be obtained by utilizing a spring having more turns, a greater outside diameter and finer wire, but the design herein has been found to be satisfactory. The ratio of change in the extension of the spring to the change in the pressure exerted by the jaws is so small that the change is inconsequential as to effect upon the measurements being made. The weight of the slide 12 and the friction between the slide 12 and the base 11 have minimal effect upon pressure applied between the nibs 20 and 21.

As seen in FIG. 1, a linear scale 57 is formed on the slide 12, as by embossments thereon, and cooperates with an embossed arrow 58 juxtaposed on the base 11 so visual identification of the distance between the nibs 20 and 21 of the respective jaw portions 15 and 18 can be made. This measurement may be denoted in millimeters, inches or the like. Typically, the thickness of a skin fold lies between 0 and 50 millimeters, i.e. 0 and 2 inches. Obviously, larger measurements could be taken and the caliper configured to accommodate such distances.

A thumb knurl, generally designated 60, is formed on the wall 51 of the slide 12 to provide a gripping surface to assist the operator in manually moving the slide 12 axially relative to the base 11. The caliper 10 may be operated with either the left or the right hand and generally is expected to be operated by one hand alone.

FIG. 1 illustrates the measurement of a skin fold 62 which has been extended from the body of tissue 63 and clamped by spring pressure between the nibs 20 and 21 of the respective jaw portions 15 and 18. The arrow 58 indicating on the linear scale 57 the thickness of the skin fold being measured.

I claim:

1. A skin-fold caliper for manipulated measuring of the thickness of a person's body and limbs skin fold comprising:

a base member having a first jaw portion adjacent one end and a handle portion defining its other end, said base member having a dovetail-shaped recess defined therein, said recess having an end open at the first jaw end and extending toward the handle end, said jaw portion having a nib facing axially outward from the first jaw end;

a slide member having a second jaw portion adjacent one end and a mounting portion defining its other end, said mounting portion having a sectional size and configuration corresponding to said recess so that said mounting portion is axially slidable therein when inserted into the open end of said recess, said base member and said slide member thereby having respective opposing surfaces slidable relative to each other, said base member having a first axially-extending channel formed in its opposing surface, said first channel opening toward said slide member and having an end open at the first jaw end, said slide member having a second axially-extending channel formed in its opposing surface, said second channel opening toward said base member opposite said first channel and having an end open at the mounting end so that said first and second channels together defining a hollow housing;

a coiled spring within said housing;

first means carried by said base member in the housing adjacent the handle end for attaching one end of said spring thereto;

second means carried by said slide member in the housing adjacent the second jaw end for attaching the other end of said spring thereto so as to urge said jaw portions closed;

gripping means integrally formed on said base member providing increased gripping capability for an operator's hand;

gripping means integrally formed on said slide member for providing increased gripping capability for an operator's thumb so that said jaw portions may be manually opened against the pressure of said spring by an operator using one hand; and scale means on said slide member and said base member juxtaposed for visual identification of the distance between said nibs thereby providing an indication of the thickness of a skin fold clamped between said nibs under spring pressure.

2. The skin-fold caliper of claim 1 wherein the spring is selected so that the pressure applied between said nibs is approximately 10 grams per square millimeter when the nibs are closed together and the ratio of change in distance in inches between the nibs to change in pressure in grams per square millimeter is greater than 0.5.

* * * * *